United States Patent
Blackburn et al.

(10) Patent No.: US 10,334,857 B2
(45) Date of Patent: Jul. 2, 2019

(54) *CHROMOBACTERIUM* SPECIES WITH INSECTICIDAL ACTIVITY

(71) Applicant: The United States of America, as represented by the Secretary of Agriculture, Washington, DC (US)

(72) Inventors: Michael B. Blackburn, Woodbine, MD (US); Dawn E. Gundersen-Rindal, Silver Spring, MD (US); Robert R. Farrar, Bowie, MD (US); Daniel J. Kuhar, Laurel, MD (US); Ashaki D. Mitchell, Mount Airy, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 56 days.

(21) Appl. No.: 15/728,901

(22) Filed: Oct. 10, 2017

(65) Prior Publication Data
US 2018/0103646 A1    Apr. 19, 2018

Related U.S. Application Data

(60) Provisional application No. 62/408,388, filed on Oct. 14, 2016.

(51) Int. Cl.
| | |
|---|---|
| *A01N 63/02* | (2006.01) |
| *A01N 25/00* | (2006.01) |
| *C12N 1/20* | (2006.01) |
| *A01N 65/00* | (2009.01) |

(52) U.S. Cl.
CPC .......... *A01N 63/02* (2013.01); *A01N 25/006* (2013.01); *C12N 1/20* (2013.01); *A01N 65/00* (2013.01)

(58) Field of Classification Search
CPC ........ C12N 1/20; A01N 25/006; A01N 63/02; A01N 65/00
See application file for complete search history.

(56) References Cited

U.S. PATENT DOCUMENTS

| | | |
|---|---|---|
| 9,259,007 B2 | 2/2016 | Asolkar et al. |
| 9,339,039 B1 | 5/2016 | Martin et al. |
| 2007/0172463 A1 | 7/2007 | Martin et al. |

OTHER PUBLICATIONS

NCBI GenBank Accession No. JF3089482; *Chromobacterium* sp. HME6876 16S ribosomal RNA gene, partial sequence, (2011).

Ramirez et al.,; *Chromobacterium* Csp_P Reduces Malaria and Dengue Infection in Vector Mosquitoes and Has Entomopathogenic and In Vitro Anti-pathogen Activities; PLOS Pathogens, (2014), 10(10):1-13.

International Searching Authority, PCT/US2017/056119 for The United States of America, as Represented by the Secretary of Agriculture, International Filing date Oct. 11, 2017.

*Primary Examiner* — Sarvamangala Devi
(74) *Attorney, Agent, or Firm* — John Fado; Ariel Atkinson

(57) ABSTRACT

A novel *Chromobacterium phragmitis* sp. nov. strain 113-1 (NRRL B-67133) is described, which has insecticidal activity against insect larvae, in general, and dipteran and lepidopteran insect larvae, in particular. A biocontrol agent containing *Chromobacterium phragmitis* sp. nov. strain 113-1 (NRRL B-67133) and optionally a carrier are also described. Methods of killing insect larvae and methods of reducing insect populations in an area by applying to the area or an object an effective amount of the biocontrol agent are also described.

10 Claims, 1 Drawing Sheet
Specification includes a Sequence Listing.

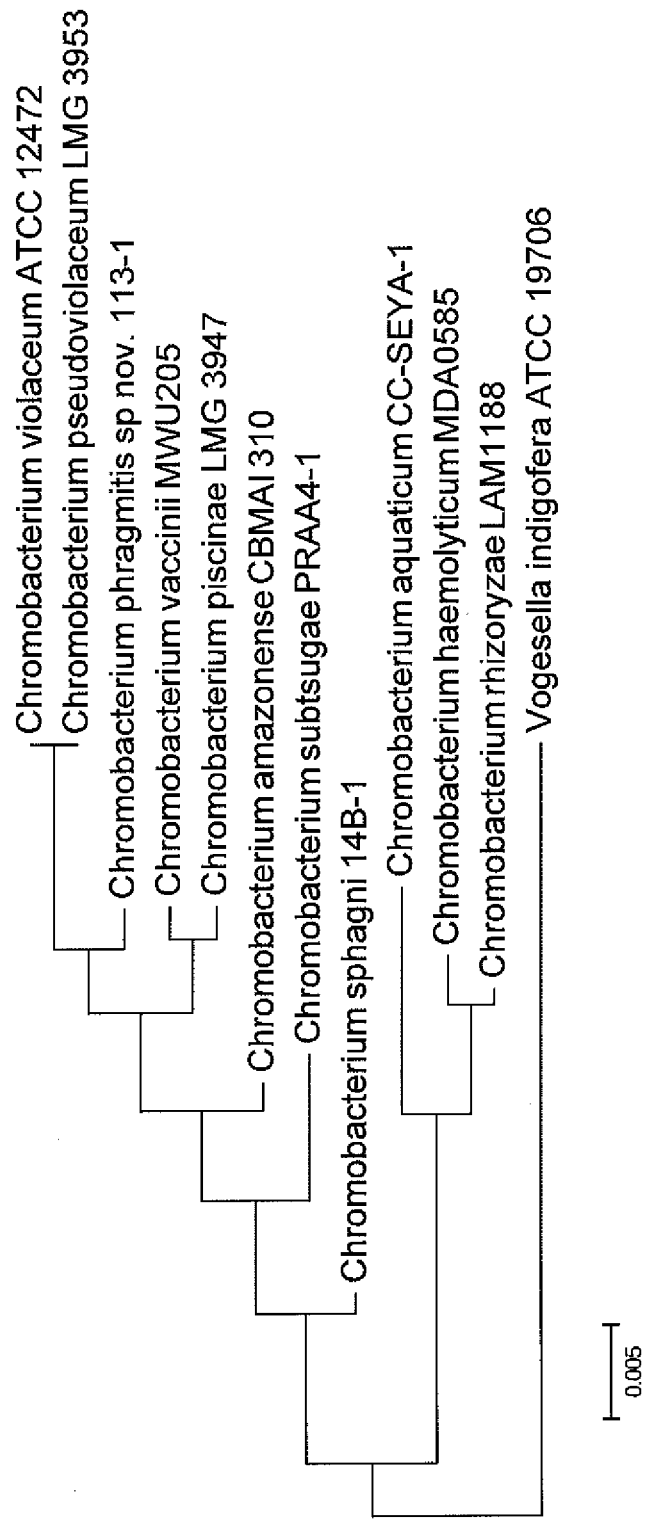

SEQUENCE LISTING

<160> NUMBER OF SEQ ID NOS: 1

<210> SEQ ID NO 1
<211> LENGTH: 1184
<212> TYPE: DNA
<213> ORGANISM: Chromobacterium phragmitii strain 113-1

<400> SEQUENCE: 1

```
ggattaatac cgcatacgcc ctgaggggga aagcggggga tcgaaagacc tcgcgttata    60
cgagcagccg atgtctgatt agctagttgg tggggtaaga gcccaccaag gcgacgatca   120
gtagcgggtc tgagaggatg atccgccaca ctgggactga gacacggccc agactcctac   180
gggaggcagc agtggggaat tttggacaat gggcgcaagc ctgatccagc catgccgcgt   240
gtctgaagaa ggccttcggg ttgtaaagga cttttgtcag ggaggaaatc ccgctggtta   300
atacctggcg gggatgacag tacctgaaga ataagcaccg gctaactacg tgccagcagc   360
cgcggtaata cgtagggtgc aagcgttaat cggaattact gggcgtaaag cgtgcgcagg   420
cggttgtgca agtctgatgt gaaagccccg ggctcaacct gggaacggca ttggagactg   480
cacgactaga gtgcgtcaga gggggtaga attccacgtg tagcagtgaa atgcgtagag   540
atgtggagga ataccgatgg cgaaggcagc cccctgggat gacactgacg ctcatgcacg   600
aaagcgtggg gagcaaacag gattagatac cctggtagtc cacgccctaa acgatgtcaa   660
ctagctgttg ggggtttgaa tccttggtag cgtagctaac gcgtgaagtt gaccgcctgg   720
ggagtacggc cgcaaggtta aaactcaaag gaattgacgg ggacccgcac aagcggtgga   780
tgatgtggat taattcgatg caacgcgaaa aaccttacct gctcttgaca tgtacggaac   840
ttggtagaga tatcttggtg cccgaaaggg agccgtaaca caggtgctgc atggctgtcg   900
tcagctcgtg tcgtgagatg ttgggttaag tcccgcaacg agcgcaaccc ttgtcattag   960
ttgccatcat taagttgggc actctaatga gactgccggt gacaaaccgg aggaaggtgg  1020
ggatgacgtc aagtcctcat ggcccttatg agcagggctt cacacgtcat acaatggtcg  1080
gtacagaggg ttgccaagcc gcgaggtgga gctaatctca gaaaaccgat cgtagtccgg  1140
atcgcactct gcaactcgag tgcgtgaagt cggaatcgct agta                   1184
```

CHROMOBACTERIUM SPECIES WITH INSECTICIDAL ACTIVITY

CROSS-REFERENCE TO PRIOR FILED APPLICATIONS

This application claims priority to U.S. Patent Application 62/408,388 filed on Oct. 14, 2016, the contents of which are incorporated herein by reference in its entirety.

SEQUENCE LISTING

The Sequence Listing submitted via EFS-Web as ASCII compliant text file format (.txt) filed on Oct. 10, 2017, named "SequenceListing_ST25", (created on Oct. 4, 2017, 2 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND OF THE INVENTION

Field of the Invention

This invention relates to a novel species of *Chromobacterium*, which is being named *Chromobacterium phragmitis* sp. nov., that has insecticidal activity. This invention also relates to compositions containing this novel *Chromobacterium* strain and use of these compositions to kill insect larvae.

Description of Related Art

The Lepidoptera is an order of insects that include moths and butterflies, while the Diptera includes flies and mosquitoes. Many species of both orders are serious agricultural pests whose feeding damages many different types of crops. While many birds and other animals feed on these pests, these predators do not sufficiently reduce the harm caused by the larvae to food crops. Parasitic wasps and entomopathogenic nematodes can also help reduce the populations of lepidopteran and dipteran pests, but again not sufficiently to reduce economic damage to crops. On the other hand, insecticides can be used to destroy populations of insects. But many of the insecticides are non-specific and harm beneficial animals, especially bees and birds. Further, the pesticides can enter groundwater and be ingested by humans, again causing harm. As such, a need exists for safer compositions that can kill pest insects and methods of protecting crops using such compositions.

Other insects also destroy economically valuable plants (crops, trees, ornamental plants) by feeding on the economically valuable plants either while in larvae stage or as an adult. It is difficult to kill many these insects or reduce their population without using pesticides that are harmful to the plant or mammals that eat the plants.

Until recently, purple-pigmented bacteria of the genus *Chromobacterium* were represented by a single species, *Chromobacterium violaceum* (Bergonzini 1881). *Chromobacterium violaceum* is best known for production of the purple pigment violacein, which has exhibited diverse antimicrobial and antitumor activities. In 2007, Martin, et al., *Int. J. Systemic and Evolutionary Micro* 57:993-999 (2007) described *Chromobacterium subtsugae*, which in addition to violacein, also produced insecticidal factors that were active against a variety of insect pests. See also U.S. Pat. No. 7,244,607. More recently, an extract of *C. subtsugae* was approved by the EPA for use as an organic insecticide that is now commercially available as Grandevo® (Marrone Biolnnovations, Davis, Calif.). Since the description of *C. subtsugae*, eight additional species of *Chromobacterium* have been described: *C. aquaticum, C. haemolyticum, C. piscinae, C. pseudoviolaceum, C. amazonense, C. vaccinii, C. rhizoryzae* and *C. sphagni. Chromobacterium vaccinii* and *C. sphagni* have also been found to produce insecticidal factors that kill insect larvae. See WO 2015/020848 and U.S. Patent Application Publication 2017/0251676.

*Bacillus thuringiensis* var. *kurstaki* (Btk) is an effective biocontrol agent for lepidoteran insects that has been in use since its discovery in 1962. However, some species of Lepidoptera have recently become resistant to the Cry toxin produced by Btk. See, Cancino-Rodenzo, et al., *Insect Biochem. Mol. Biol.* 40:58-63 (2010). While *Bacillus thuringiensis* var. *israelensis* (Bti) can be used to successfully control mosquitoes, blackflies, and fungus gnats, other dipteran species are not susceptible to the bacteria, and the development of resistance among susceptible insects is a concern. Thus, a need exists for additional biocontrol agents that can selectively kill insects in general, and more specifically lepidopteran and dipteran species.

BRIEF SUMMARY OF THE INVENTION

It is an object of this invention to have a biocontrol agent useful for killing lepidopteran insect larvae and dipteran insect larvae. This biocontrol agent contains an insecticidal composition which can be *Chromobacterium phragmitis* strain 113-1 (NRRL B-67133), media in which *C. phragmitis* strain 113-1 (NRRL B-67133) grew, or a combination thereof.

It is another object of this invention to have a biocontrol agent useful for killing insect larvae (lepidopteran insect larvae and dipteran insect larvae). This biocontrol agent contains a carrier and an insecticidal composition which can be *Chromobacterium phragmitis* strain 113-1 (NRRL B-67133), media in which *C. phragmitis* strain 113-1 (NRRL B-67133) grew, or a combination thereof. The insecticidal composition kills an insect that ingests it. This biocontrol agent can be a pellet, wettable powder, dust, granule, adherent dust or granule, solution, emulsifiable concentrate, emulsion, suspension concentrate, aerosol, and/or bait. It is also an object of this invention that the carrier can be food which insect larvae (lepidopteran insect larvae and dipteran insect larvae) eat, water, one or more surfactants, one or more emulsifiers, one or more alcohols, one or more oils, one or more glycerols, one or more biological buffers, one or more ethers, one or more glycols, one or more ketones, one or more esters, one or more clays, one or more silicas, one or more cellulosics, one or more rubber, one or more synthetic polymers, or a combination thereof. The biocontrol agent can be further formulated with insect attractants, such as pheromones, insect extracts containing pheromones, or other non-pheromone compounds known to attract the target insects.

It is an object of this invention to have a method for killing insect larvae by applying a biocontrol agent in an amount effective to kill the insect larvae (lepidopteran insect larvae and dipteran insect larvae). This biocontrol agent contains an optional carrier and an insecticidal composition. It is a further object of this invention that the insecticidal composition contains *C. phragmitis* strain 113-1 (NRRL B-67133), media in which *C. phragmitis* strain 113-1 (NRRL B-67133)

grew, or a combination thereof. The insecticidal composition kills an insect that ingests it. Another object of this invention is that the biocontrol agent is applied to an area in which the insect larvae (lepidopteran insect larvae and dipteran insect larvae) are present (or are expected to be present) or onto an object in the area. In one embodiment of this invention, the object is a plant on which the insect larvae live or which the insect larvae eats. In a further object of this invention, the insect larvae are lepidopteran or dipteran insect larvae. It is also an object of this invention that the carrier can be food which insect larvae eat, water, one or more surfactants, one or more emulsifiers, one or more alcohols, one or more oils, one or more glycerols, one or more biological buffers, one or more ethers, one or more glycols, one or more ketones, one or more esters, one or more clays, one or more silicas, one or more cellulosics, one or more rubber, one or more synthetic polymers, or a combination thereof. Another object of the invention is that the biocontrol agent can also contain one or more insect larvae attractants, one or more adjuvants, one or more pheromones, one or more adhesives, one or more dispersants, or a combination thereof.

It is an object of this invention to have a method of reducing the population of insect larvae (lepidopteran insect larvae and dipteran insect larvae) by applying a biocontrol agent to an area in which the insect larvae are present or onto an object in the area in an amount effective to kill the insect larvae thereby reducing the population of the insect larvae. It is a further object of this invention that the biocontrol agent contains a carrier and an insecticidal composition where the insecticidal composition can be C. phragmitis strain 113-1 (NRRL B-67133), media in which C. phragmitis strain 113-1 (NRRL B-67133) grew, or a combination thereof. The insecticidal composition kills an insect that ingests it. It is an optional object of this invention that the object is a plant on which the insect larvae live or eat. It is another object of this invention that the insect larvae are lepidopteran or dipteran insect larvae. It is also an object of this invention that the carrier can be food which insect larvae eat, water, one or more surfactants, one or more emulsifiers, one or more alcohols, one or more oils, one or more glycerols, one or more biological buffers, one or more ethers, one or more glycols, one or more ketones, one or more esters, one or more clays, one or more silicas, one or more cellulosics, one or more rubber, one or more synthetic polymers, or a combination thereof. Another object of the invention is that the biocontrol agent can also contain one or more insect larvae attractants, one or more adjuvants, one or more pheromones, one or more adhesives, one or more dispersants, or a combination thereof.

It is a further object of this invention to have a composition containing C. phragmitis strain 113-1 (NRRL B-67133). It is a further object of this invention to use this composition to kill lepidopteran insect larvae and dipteran insect larvae that ingest this composition.

BRIEF DESCRIPTION OF THE SEVERAL VIEWS OF THE DRAWINGS

FIG. 1 shows the maximum likelihood analysis of 16S rRNA gene sequences from Chromobacterium phragmitis sp. nov. isolate 113-1 with 16S rRNA gene sequences of recognized Chromobacterium species. Vogesella indigofera is included as an outgroup.

STATEMENT REGARDING DEPOSIT OF BIOLOGICAL MATERIAL UNDER THE TERMS OF THE BUDAPEST TREATY

On or before Sep. 10, 2015, the inventors deposited a sample of novel Chromobacterium phragmitis sp. nov. strain 113-1 as described herein, with the U.S.D.A., Agricultural Research Service's Patent Culture Collection located at the National Center for Agricultural Utilization Research, 1815 N. University Street, Peoria, Ill. 61604, in a manner affording permanence of the deposit and ready accessibility thereto by the public if a patent is granted. The deposit has been made under the terms of the Budapest Treaty on the International Recognition of the Deposit of Microorganisms for the Purposes of Patent Procedure and the regulations thereunder. C. phragmitis sp. nov. strain 113-1 has the deposit's accession number NRRL B-67133.

All restrictions on the availability to the public of Chromobacterium phragmitis sp. nov. strain 113-1 (NRRL B-67133) which has been deposited as described herein will be irrevocably removed upon the granting of a patent covering these particular biological materials.

The Chromobacterium phragmitis sp. nov. strain 113-1 (NRRL B-67133) has been deposited under conditions such that access to the microorganism is available during the pendency of the patent application to one determined by the Commissioner to be entitled thereto under 37 C.F.R. § 1.14 and 35 U.S.C § 122.

The deposited biological material will be maintained with all the care necessary to keep it viable and uncontaminated for a period of at least five years after the most recent request for the furnishing of a sample of the deposited microorganisms, and in any case, for a period of at least thirty (30) years after the date of deposit for the enforceable life of the patent, whichever period is longer.

We, the inventors for the invention described in this patent application, hereby declare further that all statements regarding this Deposit of the Biological Material made on information and belief are believed to be true and that all statements made on information and belief are believed to be true, and further that these statements are made with knowledge that willful false statements and the like so made are punishable by fine or imprisonment, or both, under section 1001 of Title 18 of the United States Code and that such willful false statements may jeopardize the validity of the instant patent application or any patent issuing thereon.

DETAILED DESCRIPTION OF THE INVENTION

Described herein is a novel Chromobacterium species, namely, Chromobacterium phragmitis sp. nov. strain 113-1 (NRRL B-67133) and cultures in which the bacteria grew. The sequence of an 1184 nucleotide internal fragment of the 16S rRNA gene of C. phragmitis sp. nov. strain 113-1 (NRRL B-67133), obtained by PCR amplification, is in SEQ ID NO: 1. The bacteria produce one or more compounds that can kill insect larvae in general, and, more specifically, dipteran and lepidopteran insect larvae. The C. phragmitis sp. nov. strain 113-1 described herein were obtained from a tidal marsh along the lower Potomac River in Charles County, Md. See Example 1, infra, for more information. Not wishing to be bound to any particular hypothesis, the C. phragmitis sp. nov. strain 113-1 (NRRL B-67133) synthesizes one or more compounds which are toxic to insect larvae. Because C. phragmitis sp. nov. strain 113-1 (NRRL B-67133) produces one or more compounds that are toxic to insect larvae, the bacteria and/or the media in which the bacteria grew are considered the insecticidal compositions of the biocontrol agents described herein.

Described herein are methods of killing insects, involving exposing (or treating) the insect larvae to the biocontrol agents described herein by applying the biocontrol agent to an object (e.g., insects, plants, fruit trees, screens and netting, traps) or an area (e.g., water, soil, house, farm land) in need of such treatment. The amount of the biocontrol agent to be applied should be sufficient to kill the insect larvae (an effective amount). Also described herein are methods of reducing insect populations by applying an effective amount of the biocontrol agent to an object or area.

The terms "object" or "area" as used herein include any place where the presence of target pests is not desirable, including any type of tree, crop, natural or artificial parkland, watercourse, or other target pest habitat. In one embodiment, the area or object where the biocontrol agent can be dispersed, placed, applied, etc., excludes tidal marshes.

The terms "object" or "area" as used herein include any place where the presence of target insect pests (e.g., species of Lepidoptera or Diptera) are not desirable, including any type of premises, which can be out-of-doors, such as in gardens, lawns, tents, camping areas, farmland, parks, etc., or indoors, such as in barns, garages, commercial buildings, homes, etc., or any area where insect pests are a problem, such as in shipping or storage containers (e.g., bags, boxes, crates, etc.), packing materials, bedding, and so forth. Also included in the definition of object or area are the outer covering of a living being, such as skin, fur, hair, or clothing. Thus, the methods include dispensing the bacteria, media in which the bacteria were grown, or biocontrol agents described herein into the area in traps, sprays, emulsions, freeze-dried blocks, coatings or vapor form (e.g., an aerosol). One may use devices that allow a slow sustained release of bacteria, media in which the bacteria were grown, and/or biocontrol agent into the environment from a sealed canister or chemical or physical (e.g., fabric) matrix. One may also use a biocontrol agent that contains a bait for the insect pest and contains the bacteria and/or media in which the bacteria were grown. The biocontrol agent can be placed in an area or on an object where insect pests are not wanted and in a manner that the larvae of the insect pests ingest the biocontrol agent. Similarly, the biocontrol agent can contain a formulation of the media in which the bacteria were grown and sprayed onto economically important plants (crops, trees, ornamental plants, etc.) or onto other objects in a manner such that the larvae of the insect pests will ingest the biocontrol agent. In one embodiment, plants that live in tidal marshes are not considered economically important plants.

One applies, at a minimum, an effective amount of a biocontrol agent containing *Chromobacterium phragmitis* sp. nov. strain 113-1 (NRRL B-67133). In an alternative embodiment, one can apply an effective amount of a biocontrol agent containing the media in which the bacteria were grown to an object or area. In this embodiment, the bacteria may still be present in the culture media. The term "effective amount," as used herein, means the minimum amount of the compositions needed to kill the insects in an area or on an object when compared to the same area or object which is untreated. The precise amount needed will, by necessity, vary in accordance with the target insect; particular composition used; the type and size of area or object to be treated; weather or climatic conditions under which it is applied; and the environment in which the area or object is located. The precise amount of the composition can easily be determined by one skilled in the art given the teachings herein.

The biocontrol agents described herein which contain an insecticidal composition and optionally a carrier. The insecticidal composition can be *Chromobacterium phragmitis* sp. nov. strain 113-1 (NRRL B-67133). The insecticidal composition may also be media in which the bacteria were grown, alone, or with the bacteria that were cultured in that media. The media may contain the bacteria or the cytosolic components of the bacteria. In one embodiment, the bacteria are grown in media until the bacteria have reached their peak growth and the number of live bacteria is decreasing. Such media is sometimes referred to as "spent media". As such, the insecticidal composition, in one embodiment, contains spent media with the bacteria described herein. In another embodiment, the bacteria are lysed, and the media is filtered to remove bacterial cell wall and membrane components. In such an embodiment, the insecticidal composition contains the spent media without whole bacteria. In yet another embodiment, the bacteria are inactivated and left in the media. In such an embodiment, the insecticidal composition contains the media and the inactivated bacteria. In another possible embodiment, the bacteria are not actively lysed, but the bacteria and the media are still separated from each other. Then one can use the media or the bacteria in the biocontrol agent. In any of these embodiments, the media can be applied in a liquid-form or freeze-dried and applied as a solid, or freeze-dried and then resuspended in another liquid or reduced volume. One another embodiment, the biocontrol agent may also contain one or more other compounds (e.g., insect larvae attractants, adjuvants, pheromones, adhesives, dispersants or other insecticidal agents known in the art) provided the one or more other compounds do not substantially interfere with the insecticidal activity or efficacy of the insecticidal composition described herein. Whether or not one or more other compounds interfere with the insecticidal activity and/or efficacy of the insecticidal compositions can be determined, for example, by the procedures utilized below. The biocontrol agent, in one embodiment, excludes liquids and plants obtained from a tidal marsh. In another embodiment, the biocontrol agent of the present invention excludes killed insects or insects that have already ingested the bacteria described herein. In another embodiment, the biocontrol agent described herein excludes water obtained from a tidal marsh or other substances obtained from a tidal marsh.

The biocontrol agent described herein can contain a carrier. The carrier may be, for example, any agronomically or physiologically or pharmaceutically acceptable carrier. The carrier as used herein, in one embodiment, does not including the body of an insect. One possible carrier is insect food. The carrier, in another embodiment, can be an insect attractant such as bait or pheromones. The carrier should not be harmful to plants and/or other non-target organisms. In some embodiments, the biocontrol agent can be insect food impregnated with one or more of the insecticidal composition described herein, or the insecticidal composition described herein can be sprayed onto insect food. One can apply such embodiments of the biocontrol agent to areas where the insect larvae live.

The bacteria and/or media are optionally used in combination with one or more carriers or additives such as water (in one embodiment, purified or distilled water), humectants, surfactants, inert carriers, other insecticides, and colorants; typical humectants, inert carriers, insecticides, and colorants are well known in the art. As a practical matter, it is expected that the bacteria will be formulated with an inert carrier for use as a pesticide composition. Such inert carriers are well known in the art. Water (purified or distilled) is one inert carrier, although other inert carriers suitable for use herein include but are not limited to inorganic or organic biological buffers, alcohols, ethers, glycols, ketones, esters, and solid carriers such as clays, silicas, cellulosics, rubber, or synthetic polymers. Surfactants are well-known in the art field and used to assist in the mixing of, for example, freeze-dried media containing bacteria and water. In one embodiment, culture medium is a carrier for the bacteria. In this embodiment, the insecticidal agent is *Chromobacterium phragmitis* sp. nov. strain 113-1 (NRRL B-67133); and the carrier is the culture media. The medium described in the examples, infra, are non-limiting examples of culture medium in which these bacteria can be grown.

A single application will suffice under optimum conditions, with mortality occurring rapidly, but under suboptimum conditions, either higher concentrations or multiple applications may be necessary.

The biocontrol agent described herein contains *Chromobacterium phragmitis* sp. nov. strain 113-1 (NRRL B-67133) and optionally one or more carriers.

In one embodiment, the biocontrol agent described herein also contains another insecticide effective for controlling species of Lepidoptera and Diptera and/or other insect species. As used herein, the term "insecticide" refers to a material or mixture of materials which induce mortality, disrupt or impede growth, interfere with metamorphosis or other morphogenic functions, effect sterilization, or interfere with feeding, metabolism, respiration, locomotion or reproduction of the targeted insects. Suitable insecticides include but are not limited to biological controls such as insect growth regulators, and materials that are toxic to insects (i.e., toxicants) such as chemical insecticides, pathogenic nematodes, fungi, protozoans, or other bacteria. In one embodiment, insecticides are slow-acting (i.e., acting over a course of hours, days, weeks, or preferably months) to reduce "avoidance" effects before individuals have distributed the insecticide to other members of the population or colony. Slow-acting insecticides are known in the art. The composition may also contain biological control agents such as toxins derived from bacteria, fungi, or other organism. One example of a biological control agent is *B. thuringiensis* toxin.

The biocontrol agents described herein may be formulated as wettable powders, dusts, granules, adherent dusts or granules, solutions, emulsifiable concentrates, emulsions, suspension concentrates, aerosols, and/or baits. The biocontrol agents may also be further formulated with insect attractants, such as pheromones, insect extracts containing pheromones, or other non-pheromone compounds known to attract the target insects.

The target insects include, but are not limited to, lepidopteran and dipteran insects, such as gypsy moth (*Lymantria dispar*), diamondback moth (*Plutella xylostella*), tobacco hornworm (*Manduca sexta*), cabbage looper (*Trichoplusia ni*), corn earworm (*Helicoverpa zea*), beet armyworm (*Spodoptera exigua*), fall armyworm (*Spodoptera frugiperda*), European corn borer (*Ostrinia nubilalis*), tobacco budworm (*Heliothis virescens*), seedcorn maggot (*Delia platura*), cabbage root fly (*Delia radicum*), carrot fly (*Chamaepsila rosae*), cranefly turf pests belonging to the genus *Tipula*, fungus gnats (family Sciaridae), stable fly (*Stomoxys calcitrans*), mosquitoes (family Culicidae) and blackflies (family Simuliidae).

The terms "approximately" and "about" refer to a quantity, level, value or amount that varies by as much as 30% in one embodiment, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria of the same species.

Many techniques involving molecular biology discussed herein are well-known to one of ordinary skill in the art and are described in, e.g., Green and Sambrook, *Molecular Cloning, A Laboratory Manual* 4th ed. 2012, Cold Spring Harbor Laboratory; Ausubel et al. (eds.), *Current Protocols in Molecular Biology*, 1994—current, John Wiley & Sons; and Kriegler, *Gene Transfer and Expression: A Laboratory Manual* (1993). Unless otherwise noted, technical terms are used according to conventional usage. Definitions of common terms in molecular biology maybe found in e.g., Benjamin Lewin, *Genes IX*, Oxford University Press, 2007 (ISBN 0763740632); Krebs, et al. (eds.), *The Encyclopedia of Molecular Biology*, Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1. Isolation of Bacteria

A new strain of *Chromobacterium phragmitis* sp. nov. that fulfills the criteria for a new species, strain 113-1 (NRRL B-67133), has been obtained. *C. phragmitis* sp. nov. strain 113-1 (NRRL B-67133) was isolated from a tidal marsh along the Potomac River in Charles County, Md.

Bacteria are isolated from water samples using a solid medium, modified from Keeble and Cross (*J. App. Microbio.* 43:2 325-327 (1977)), containing 1 g yeast extract, 3 g nutrient broth, 10 g glucose, 18 g agar, and 50 mg each of the antibiotics neomycin and cycloheximide per liter of water. Plates are incubated at 24° C. for 48 hours to 72 hours. Potential colonies of *Chromobacterium* are selected based on violet colony color. Bacteria used for insect bioassays are then grown in a liquid medium with the same components listed above but without agar or antibiotics. Liquid cultures are shaken at 200 rpm and 24° C. for 96 hours.

Example 2. Genetic and Biochemical Analyses of Bacteria

PCR amplification and sequencing of the 16S rRNA genes from *C. phragmitis* sp. nov. strain 113-1 (NRRL B-67133) resulted in an 1184 nucleotide sequence (SEQ ID NO: 1). The complete DNA sequences of *C. phragmitis* sp. nov. strain 113-1 (NRRL B-67133) 16S rRNA genes have not yet been obtained.

Using SEQ ID NO: 1, maximum likelihood analysis can be used to create a depiction of how *C. phragmitis* sp. nov. strain 113-1 (NRRL B-67133) is related to the type strains of other currently recognized *Chromobacterium* species (*C. violaceum, C. subtsugae, C. vaccinii, C. piscinae, C. aquaticum, C. pseudoviolaceum, C. haemolyticum, C. amazonense, C. rhizoryzae,* and *C. sphagni* sp. nov.). See FIG. 1.

Like the other insecticidal *Chromobacterium* species (*C. vaccinii* MWU205$^T$, *C. subtsugae* PRAA4-1$^T$, and *C. sphagni* 14B-1) *C. phragmitis* sp. nov. strain 113-1 (NRRL B-67133) produces arginine dihydrolase and protease, can assimilate glucose, N-acetylglucosamine and gluconate, does not produce urease or β-galactosidase, and does not assimilate arabinose, mannitol, maltose, adipic acid or phenylacetic acid. Unlike all the aforementioned insecticidal species, *C. phragmitis* sp. nov. strain 113-1 (NRRL B-67133) produces β-glucosidase. Unlike *C. subtsugae* PRAA4-1$^T$ and *C. sphagni* 14B-1, *C. phragmitis* sp. nov. strain 113-1 (NRRL B-67133) can assimilate trisodium citrate; unlike *C. subtsugae* PRAA4-1$^T$, *C. phragmitis* sp. nov. strain 113-1 (NRRL B-67133) was able to reduce nitrate to nitrite.

Fatty acid analysis of *C. phragmitis* sp. nov. strain 113-1 (NRRL B-67133) using the MIDI system reveals that the combined 16:1 w7c/16:1 w6c fatty acids account for 37.36% of total fatty acid content. The fraction of these particular lipids is significantly lower than levels reported for other insecticidal *Chromobacterium* species (*C. subtsugae* PRAA4-1, 41.9%; *C. vaccinii* MWU205, 41.9%; *C. sphagni* 14B-1, 45.8%). Conversely the proportion of C18:w7c fatty acid found in *C. phragmitis* sp. nov. strain 113-1 (NRRL B-67133) was 19.84%, which is substantially higher than values for *C. subtsugae* PRAA4-1$^T$ (10.62%), *C. vaccinii* MWU205$^T$ (12.63%), or *C. sphagni* 14B-1 (10.33%).

Example 3. Insecticidal Activity

*Chromobacterium phragmitis* sp. nov. 113-1 (NRRL B-67133) was found to be active against diamondback moth, cabbage looper, tobacco hornworm, and seedcorn maggot, representing insects of the orders Lepidoptera and Diptera. While the insecticidal activity of *C. phragmitis* sp. nov. strain 113-1 (NRRL B-67133) was somewhat less than that of *C. subtsugae* PRAA4-1$^T$ against diamondback moth, *C. phragmitis* sp. nov. strain 113-1 (NRRL B-67133) had greater activity against cabbage looper and tobacco hornworm than did *C. subtsugae* 205-1. *Chromobacterium phragmitis* sp. nov. strain 113-1 (NRRL B-67133) appeared somewhat more active against seedcorn maggot than *C. subtsugae* PRAA4-1$^T$. Against seedcorn maggot, *C. phragmitis* sp. nov. strain 113-1 (NRRL B-67133) was comparable to *C. vaccinii* 21-1.

For diamondback moth, cabbage looper, tobacco hornworm, and seedcorn maggot, freeze dried pellets of insect diet are rehydrated with whole liquid cultures of *C. phragmitis* sp. nov. strain 113-1 (NRRL B-67133), *C. subtsugae* PRAA4-1$^T$, *C. subtsugae* 205-1, *C. vaccinii* 21-1, or water (negative control) and are fed to the insect larvae. For diamondback moth assays, the diet is as described by Bell, et al. (Development of mass rearing technology. In *The gypsy moth: Research toward integrated pest management*. Doane and McManus (eds.), U.S. Department of Agriculture Technical Bulletin 1584, Washington, pp 599-633.1981). For the cabbage looper, the diet of King and Hartley (*Heliothis virescens*. In *Handbook of Insect Rearing, vol II*. Singh and Moore (eds.), Elsevier, New York, pp. 323-328. 1985) is used. For the tobacco hornworm, the diet used is that of Martin and Blackburn, *Biol. Control* 42:226-232 (2007). For seedcorn maggot assays an artificial medium containing 50 g ground lima beans, 1.35 g meat and bone meal, and 10 g agar in 500 ml water is used. For all insects tested, hot diet is poured into 96-well ELISA plates with a volume of 300 μl per well, allowed to cool, and frozen. Diet is then freeze dried, and the resulting pellets removed from the ELISA plates. Liquid cultures are grown at 24° C. for 96 hours while shaking at 200 rpm. Assays comparing toxicities of different *Chromobacterium* strains and species are conducted contemporaneously. Data are normalized by arcsine transformation and are analyzed by analysis of variance. When significant treatment effects are found, means are separated by the least significant difference (LSD) test. See Table 2, below, for comparison of the insecticidal activity of *C. phragmitis* sp. nov. strain 113-1 (NRRL B-67133) with *C. subtsugae* PRAA4-1$^T$, *C. subtsugae* 205-1, and *C. vaccinii* 21-1.

TABLE 2

| Treatment | Diamondback moth % pupation† | Cabbage looper % mortality* | Tobacco hornworm % mortality** | Seedcorn maggot % pupation† |
|---|---|---|---|---|
| Control | 89.6 ± 3.18 A | 8.3 | 5 | 63.5 ± 9.06 A |
| *C. vaccinii* 21-1 | not tested | not tested | not tested | 2.1 ± 1.20 C |
| *C. phragmitis* 113-1 | 55.6 ± 6.15 B | 100 | 100 | 2.1 ± 1.20 C |
| *C. subtsugae* PRAA4-1$^T$ | 30.6 ± 7.50 C | not tested | not tested | 9.4 ± 5.48 B |
| *C. subtsugae* 205-1 | not tested | 12.5 | 30 | not tested |

†Data shown are mean percentage of insects pupating ± standard error (5 replicates of 24 insects per replicate). Within each insect/experiment, data followed the same letters are not considered significantly different at P = 0.05.
*24 larvae per treatment.
**20 larvae per treatment In another embodiment of this invention, a formulation of a biocontrol agent composition containing *Chromobacterium phragmitis* sp. nov. strain 113-1 is a wettable powder produced by combining a spray dried liquid fermentation media of the bacterium (containing the bacterium) with water containing emulsifiers and surfactants that promote dispersal and suspension of the spray dried powder in the water, and also promote wetting of leaf surfaces. One applies this biocontrol agent to leaf surfaces. When an insect feeds on the leaf, the insect ingests the *C. phragmitis* strain(s) and dies.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

We, the inventors, claim as follows:

1. A method of killing insect larvae comprising applying a biocontrol agent in an amount effective to kill said insect larvae, wherein said biocontrol agent comprises a carrier and an insecticidal composition selected from the group consisting of isolated *Chromobacterium phragmitis* strain 113-1 deposited with the accession number NRRL B-67133, culture media in which said *C. phragmitis* strain grew, and a combination thereof, wherein said biocontrol agent is applied to an area in which said insect larvae are present or onto an object in said area and wherein said insecticidal composition comprised in the biocontrol agent kills said insect larvae after said insect larvae ingests said insecticidal composition.

2. The method of claim 1, wherein said object is a plant on which said insect larvae live or a plant that is eaten by said larvae.

3. The method of claim 1, wherein said insect larvae are lepidopteran insect larvae and dipteran insect larvae.

4. The method of claim 1, wherein said carrier is selected from the group consisting of food of said insect larvae, water, one or more surfactants, one or more emulsifiers, one or more alcohols, one or more oils, one or more glycerols, one or more biological buffers, one or more ethers, one or more glycols, one or more ketones, one or more esters, one or more clays, one or more silicas, one or more cellulosics, one or more rubber, one or more synthetic polymers, and a combination thereof.

5. The method of claim 1, wherein said biocontrol agent further comprises at least one of insect larvae attractant, adjuvant, pheromone, adhesive, and dispersant.

6. A method of reducing the population of insect larvae comprising applying a biocontrol agent in an amount effective to kill said insect larvae thereby reducing the population of said insect larvae, wherein said biocontrol agent comprises a carrier and an insecticidal composition selected from the group consisting of isolated *C. phragmitis* strain 113-1, deposited with the accession number NRRL B-67133, culture media in which said *C. phragmitis* strain grew, and a combination thereof, wherein said biocontrol agent is applied to an area in which said insect larvae are present or onto an object in said area and wherein said insecticidal composition comprised in the biocontrol agent kills said insect larvae after said insect larvae ingests said insecticidal composition, wherein the reduction in the population of the insect larvae in said area or on said object in the area is when compared to a corresponding area or object in said corresponding area that is untreated with said biocontrol agent.

7. The method of claim 6, wherein said object is a plant on which said insect larvae live or a plant that is eaten by said insect larvae.

8. The method of claim 6, wherein said insect larvae are lepidopteran insect larvae and dipteran insect larvae.

9. The method of claim 6, wherein said carrier is selected from the group consisting of food of said insect larvae, water, one or more surfactants, one or more emulsifiers, one or more alcohols, one or more oils, one or more glycerols, one or more biological buffers, one or more ethers, one or more glycols, one or more ketones, one or more esters, one or more clays, one or more silicas, one or more cellulosics, one or more rubber, one or more synthetic polymers, and a combination thereof.

10. The method of claim 6, wherein said biocontrol agent further comprises at least one of insect larvae attractant, adjuvant, pheromone, adhesive, and dispersant.

\* \* \* \* \*